(12) United States Patent
Lacaze (10) Patent No.: US 11,426,221 B2
(45) Date of Patent: Aug. 30, 2022

(54) OSSEOUS ANCHORING IMPLANT WITH FACILITATED EXTRACTION

(71) Applicant: LOCK IN SA, Rolle (CH)

(72) Inventor: Guillaume Lacaze, La Rippe (CH)

(73) Assignee: LOCK IN SA, Rolle (CH)

( * ) Notice: Subject to any disclaimer, the term of this patent is extended or adjusted under 35 U.S.C. 154(b) by 10 days.

(21) Appl. No.: 17/093,871

(22) Filed: Nov. 10, 2020

(65) Prior Publication Data

US 2021/0315618 A1  Oct. 14, 2021

(30) Foreign Application Priority Data

Apr. 9, 2020 (FR) ...................................... 2003581

(51) Int. Cl.
  *A61B 17/84* (2006.01)
  *A61B 17/86* (2006.01)
  *A61B 17/88* (2006.01)
(52) U.S. Cl.
  CPC ........ *A61B 17/844* (2013.01); *A61B 17/8625* (2013.01); *A61B 17/8685* (2013.01); *A61B 17/8886* (2013.01)
(58) Field of Classification Search
  CPC .......................... A61B 17/844; A61B 17/8685
  See application file for complete search history.

(56) References Cited

U.S. PATENT DOCUMENTS

2008/0039846 A1* 2/2008 Lee ...................... A61B 17/686
                                                          606/63

FOREIGN PATENT DOCUMENTS

EP         2603163 A1   6/2013
WO    2012045787 A1   4/2012

* cited by examiner

*Primary Examiner* — Olivia C Chang
(74) *Attorney, Agent, or Firm* — Hauptman Ham, LLP (57) ABSTRACT

An osseous anchoring implant with facilitated extraction having: an expandable sleeve extending between a proximal portion, and a distal portion, defining a longitudinal axis, a screw extending between a proximal portion and a distal portion on an axis collinear with the axis, having an external profile complementary to the internal profile of said expandable sleeve, the screw comprising at least one distance marker to visualize the moment when the screwing of the screw in the expandable sleeve must be carried out in the opposite direction to the screwing of the expandable sleeve. The implant switches from a folded rest position to a deployed position by the penetration of the screw in the expandable sleeve. The distal portion including self-tapping notches. The distal portion includes a self-milling head.

14 Claims, 8 Drawing Sheets

OSSEOUS ANCHORING IMPLANT WITH FACILITATED EXTRACTION

RELATED APPLICATIONS

The present application claims the priority of French Application No. 2003581, filed Apr. 9, 2020, which is incorporated herein by reference in its entirety.

TECHNICAL FIELD AND OBJECT OF THE INVENTION

The present invention relates to the field of osseous implants for dental, orthopedic, surgical or osteoplastic applications, such as orthopedic screws alone or with plates, dental or ligament implants for joints such as for example the hips, the elbows, the ankles, the shoulders and the knees, or rachidian spinal implants for example for the vertebrae. These fields of application are given by way of example and are not restrictive as to the scope of the present invention.

More specifically, the invention relates to an osseous implant whose implantation in the porous bone is extremely stable.

STATE OF THE ART

An osseous anchoring implant generally consists of an elongate body intended to be implanted in a housing formed in an osseous tissue, such as the jaw bone for a dental application or in a vertebra for example.

It is important that the osseous anchoring implant can be easily introduced into the osseous tissue, without creating damage, and that the anchoring device inside the osseous tissue is stable. Indeed, current osseous anchoring implant devices do not allow anchoring without generating more cracks or damage than required for the size of the device itself in the osseous tissue, moreover it is necessary that the fixation in the osseous implant is reliable and extremely stable, because many therapeutic techniques today rely on bone growth that generally requires that the devices anchored in the osseous tissue remain as immobile as possible.

In addition, it is also necessary that the implantation in the osseous tissue is easy to perform in order to avoid any risk of incorrect positioning of the osseous anchoring implant, which could in particular be due to a difficulty in the positioning or in the implantation in the bone.

In addition, in the event of a fall, impact or accident, it is important that the osseous anchoring implant remains in place in the osseous tissue, that is to say it does not move through the bone. For this, a very high stability of the implant is necessary.

It is also important that the removal of the implant from the osseous tissue where it is implanted is possible and easily achievable, without creating injuries or damage in the osseous tissue.

The state of the art comprises the patent document EP2603163 B1, which describes an endosseous implant with improved anchoring able to be implanted in an osseous tissue and including a fixing device comprising a part called gripping part in the osseous tissue, and a part called expansion part, these two parts being movable relative to each other. The invention mentioned in this patent also comprises cooperating mechanical connection means disposed, on the one hand, on the gripping part and, on the other hand, on the expansion part, such that the relative mobility of the two parts comprises at least one degree of freedom and such that a relative displacement of said two parts causes a widening of the gripping part, said widening causing the gripping of the gripping part in the osseous tissue. The osseous implant described in this patent particularly finds application in the dental field.

However, such a solution has drawbacks because the osseous implant, although immobilized in rotation and in translation in the tissue, presents the risk of moving, in particular of receding during an impact, subsequently making its removal less easy.

The invention therefore aims at solving these drawbacks by proposing an osseous anchoring implant able to be implanted and immobilized in the osseous tissue in an extremely stable manner, then to be unscrewed and removed from the osseous tissue if necessary, without creating lesions in the osseous tissue.

GENERAL PRESENTATION OF THE INVENTION

The present invention therefore aims at overcoming the drawbacks of the prior art by proposing an osseous anchoring implant, hereinafter called osseous implant, which is easily implantable in the osseous tissue, stable and also easily removable from the osseous tissue.

To achieve this result, the present invention relates to an osseous anchoring implant with facilitated extraction, comprising:

An expandable sleeve extending between a proximal portion having a first internal diameter, and a distal portion having a second internal diameter smaller than said first internal diameter, these two portions defining a longitudinal axis (L) and said first and second internal diameters defining an internal profile of said expandable sleeve, and comprising, on the one hand, at least a first threading inside the expandable sleeve and, on the other hand, at least a second threading outside the expandable sleeve, A screw extending between a proximal portion and a distal portion on an axis collinear with the axis (L) and having, on the one hand, along said longitudinal axis (L), an external profile complementary to said internal profile of said expandable sleeve and, on the other hand, at least one external threading whose screw pitch is reversed relative to said second external threading of the expandable sleeve, The implant being able to switch from a folded rest position to a deployed position by the actuation of said reversed threadings by causing the penetration of the screw into the expandable sleeve and generating the expansion of said expandable sleeve by deformation, thanks to the fact that the external diameter of the screw is greater, at least on a distal portion, than said second internal diameter of the expandable sleeve, In the deployed position of the implant, the second internal diameter of the expandable sleeve being greater than or equal to the first internal diameter, The distal portion including a head comprising at least one rear flute with a cutting edge to mill the bone during the extraction of the osseous implant and facilitate the removal of the implant.

According to one feature, the cutting edge of said rear flute has an angle, relative to the longitudinal axis (L), determined by the thread direction of the screw when the implant is removed.

According to another feature, the external diameter of the screw is greater than the internal diameter of the sleeve, by at least one narrowing on a distal portion.

According to another feature, said at least one narrowing is located, relative to the proximal portion and along the longitudinal axis (L), at a distance determined as a function of the depth, in the osseous tissue, at which said expansion is desired.

According to another feature, the implant comprises an outer osseous anchoring threading on a frustoconical portion whose flaring is reversed relative to the flaring formed by the truncated cone of the sleeve in the deployed position.

According another feature, said expandable sleeve includes longitudinal through-slots extending up to its distal portion.

According another feature, the distal portion of the sleeve is self-tapping due to the fact that it includes at least one notch or flute.

According to another feature, there are as many self-tapping notches or flutes as there are longitudinal through-slots.

According to another feature, said expandable sleeve includes longitudinal non-through slots.

According to another feature, said screw comprises at least one distance marker to visualize the moment when the screwing of the screw in the expandable sleeve must be carried out in the opposite direction to the screwing of the expandable sleeve into the osseous tissue.

According to another feature, said at least one distance marker is a laser marker.

According to another feature, said expandable sleeve is made of plastic or elastic material.

The invention also relates to a method for extracting an osseous implant as briefly described above, the method comprising the following steps:

Unscrewing the osseous implant in the direction of the external threading until the appearance of a distance marker, Locking the implant by a clamp blocking the screw in the expandable sleeve in the rest position, Unscrewing the implant in the direction of the second threading.

According to one feature, the method comprises an additional screwing before unscrewing the osseous implant.

PRESENTATION OF THE FIGURES

Other characteristics and advantages of the invention will appear upon reading the detailed description of the embodiments of the invention, given by way of example only, and with reference to the drawings which show.

DETAILED DESCRIPTION OF ONE EMBODIMENT OF THE INVENTION

Various embodiments of the invention are described below in particular with reference to the illustrative and non-limiting figures.

The present application relates to the extraction of an osseous implant from the osseous tissue.

It may happen that the presence of an osseous implant is no longer necessary in the osseous tissue or that it is necessary to take off this osseous implant.

It should be noted here that the term "extraction" designates that fact of removing the osseous implant from the osseous tissue, generally by unscrewing, if necessary. The extraction proposed in the present application designates a removal of this osseous implant from the osseous tissue by limiting the damage related to this removal, when an ablation is desired.

In addition, the term "osseous tissue(s)" generally designates all types of bones, whether they are compact bones (such as the cortical bone or the periosteum) or cancellous (soft, porous) bones, because the osseous implant system of the present application is implantable in any type of osseous tissue.

In addition, the terms used should not be interpreted in their general meaning but rather in the light of the functional considerations detailed in the present application.

Figure 1A:
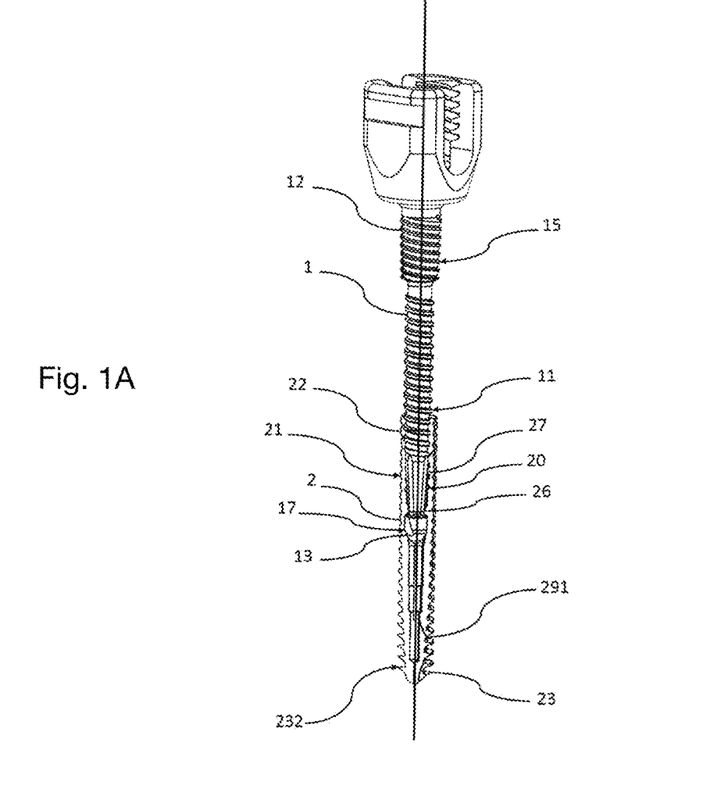
FIG. 1A, FIG. 1B and FIG. 2 represent a detailed view of the elements that make up the osseous implant according to the invention.
Figure 1B:
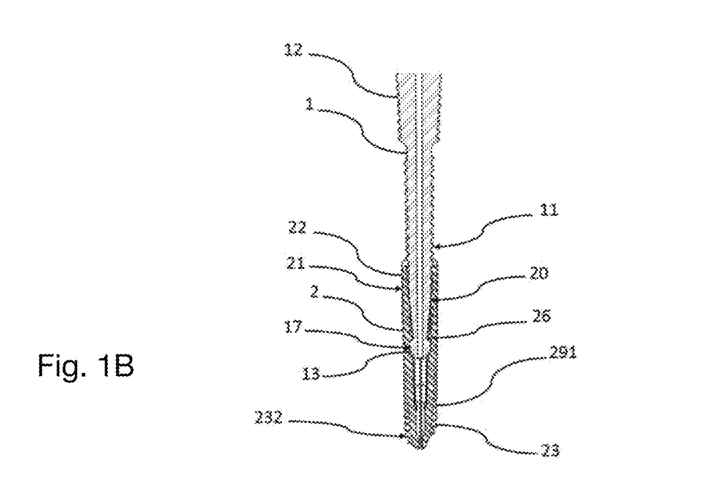

FIG. 1A and FIG. 1B are an illustrative and non-limiting exemplary embodiment of the osseous implant.

As for example represented in FIG. 1A to FIG. 11, an osseous implant able to be implanted in an osseous tissue comprises an expandable sleeve (2) extending between a proximal portion (22) having a first diameter, and a distal portion (23) having a second diameter, these two portions defining a longitudinal axis (L), and comprising, on the one hand, at least a first threading (20) inside the expandable sleeve (2) and, on the other hand, at least a second threading (21) outside the expandable sleeve (2), said expandable sleeve (2) including longitudinal through-slots (24) extending up to its distal portion (23) and self-tapping notches (231), as well as longitudinal non-through slots (25).

In the present application, the term "expandable sleeve (2)" generally designates a hollow generalized cylinder.

In some embodiments, the osseous implant also comprises a screw (1) extending between a proximal portion (12) and a distal portion (13) on an axis collinear with the axis (L) and having, on the one hand, along said longitudinal axis (L), an external profile complementary to the internal profile of said expandable sleeve (2) and, on the other hand, at least one external threading (11) whose screw pitch is reversed relative to said second external threading (21) of the expandable sleeve (2), said screw (1) comprising at least one distance marker (16) to visualize the moment when the screwing of the screw (1) in the expandable sleeve (2) must be carried out in the opposite direction to the screwing the expandable sleeve (2) into the osseous tissue The terms "proximal" and "distal" designate in the present application, respectively, the part where the implantation device is held to allow its implantation in the osseous tissue, and the part which is implanted first in the osseous tissue (opposite the proximal portion).

The terms "proximal and distal portions" designate in the present application the parts located in the vicinity of the distal and proximal ends.

It should be noted that the proximal portion (12) of the screw (1) is directly implanted in the cortical bone.

It should also be noted that the osseous implant is made of titanium or of implantable medical stainless steel or of polyetheretherketone (PEEK) or of polyetherketoneketone (PEKK) or any other material of which those skilled in the art can determine the suitability depending on its mechanical, physico-chemical properties and on its biocompatibility.

In some embodiments, the implant is able to switch from a folded rest position to a deployed position by the actuation of said reversed threadings by causing the penetration of the screw (1) into the expandable sleeve (2) and by generating the expansion of said expandable sleeve (2) by deformation, thanks to the fact that the external diameter of the screw (1) is greater than the internal diameter of the expandable sleeve (2) at least on a distal portion. In the deployed position of the implant, the second diameter of the expandable sleeve (2) is greater than or equal to the first diameter.

In some embodiments, the proximal end of the screw (1) comprises an actuating means making it possible to screw the screw (1), said actuating means comprising a structure of any shape desirable by the practitioner depending on the use which will be made of it, as for example represented in [FIG. 1b]. The actuating means being for example a hexagonal hole or a torx or a cruciform or any other actuating means, and the proximal end of the screw (1) may have various shapes depending on the desirable destination for the osseous anchoring implant (head for fixing a polyaxial or non-polyaxial osteosynthesis bar, or for fixing a plate or any other device).

In some embodiments, the screw (1) comprises a cannula passing through the screw (1) to allow the practitioner to inject for example cement, if he considers it necessary.

Figure 2:
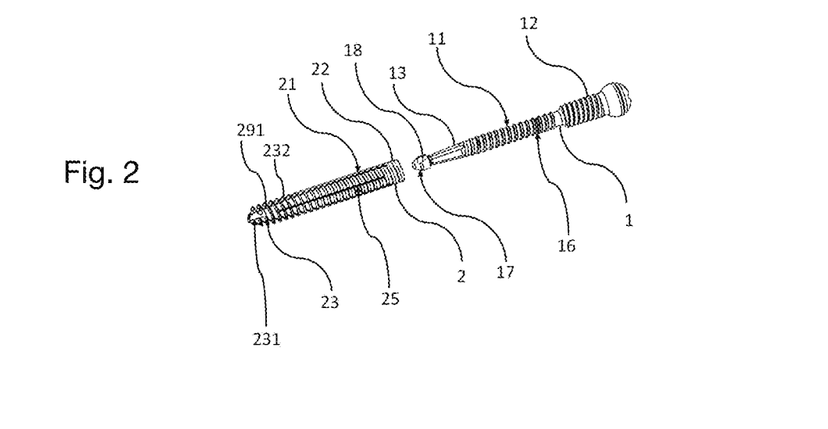

In some embodiments, the implant also comprises an outer osseous anchoring threading (15) on a frustoconical portion, as represented for example in FIG. 1A, FIG. 1B and FIG. 2.

The term "osseous anchoring" used in the present application generally designates various types of devices comprising at least one element intended to enter the osseous tissue along a rectilinear path, under the action of a push generally exerted in the form of repeated screwing operations, impacts or strikes. It is known that an osseous anchoring threading has a thread height generally greater than that of a mechanical threading to ensure better anchoring. In addition, an osseous anchoring threading is generally different from a mechanical threading and those skilled in the art know that, depending on the type of bone and desired application, it is possible to vary the diameter of the core, the screw pitch and the wire height and the present application covers these various embodiments.

In some embodiments, the external profile of the screw (1) and the internal profile of the expandable sleeve (2) are complementary, so that they provide, in an expanded configuration:

A proximal bearing point supported by the complementarity of the outer diameter of the screw (1) with the inner diameter of the expandable sleeve (2), A distal bearing point supported by the cooperation between the expandable sleeve (2) whose inner diameter narrows towards the distal portion until becoming smaller than the outer diameter of the screw (1), A "central" bearing point located between these two bearing points, formed by the cooperation between the outer diameter of the screw (1) and the inner diameter of the expandable sleeve (2) which induce an outer diameter of the expandable sleeve (2) at the "central" level which is greater than the outer diameter of the expandable sleeve (2) at the proximal bearing point.

Figure 3A:
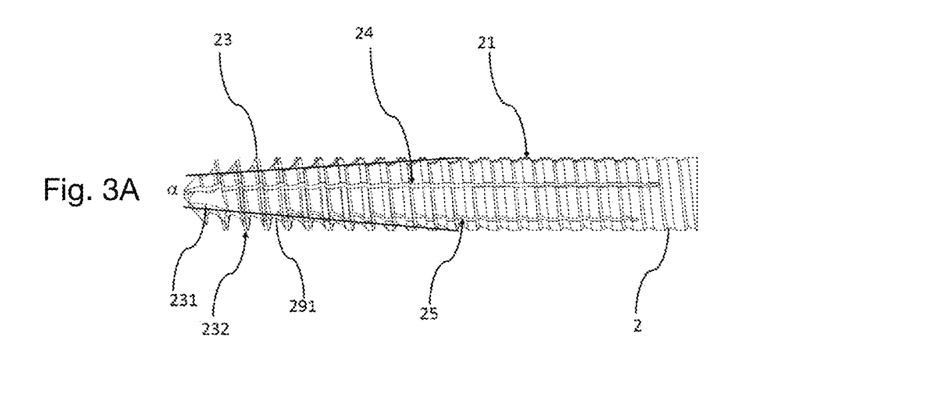
FIG. 3A represents a diagram of the sleeve of the osseous implant before the expansion according to the invention.

In some embodiments, as for example represented in FIG. 3A, the expandable sleeve (2) has an acute angle α at the end of its distal portion (23). This angle α opens and increases as the screw (1) enters the expandable sleeve (2), during the expansion.

Figure 3B:
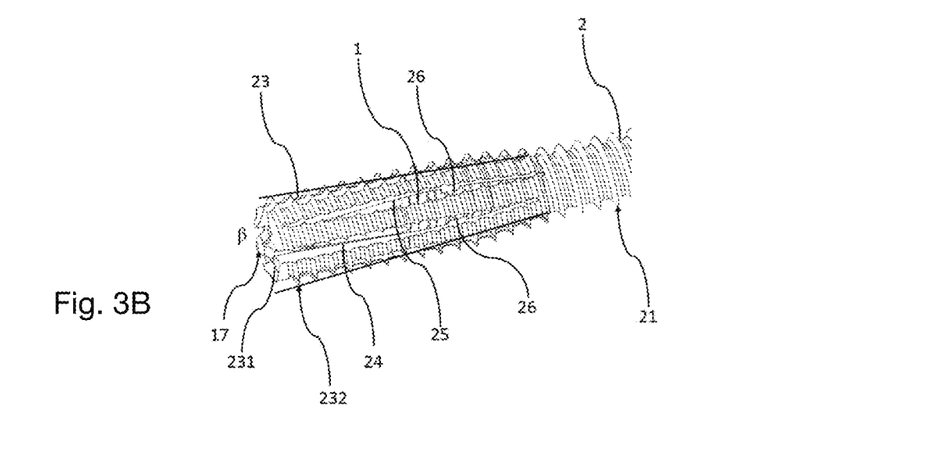
FIG. 3B represents a diagram of the sleeve of the osseous implant after the expansion according to the invention.

In some embodiments, as for example represented in FIG. 3B, the angle α, opening increasingly during the expansion, becomes an angle β, the angle β being the angle of the expanded expandable sleeve (2).

It will be noted that in the deployed position, the walls of the expandable sleeve (2) can in some embodiments be parallel instead of creating an angle β.

Figure 3C:
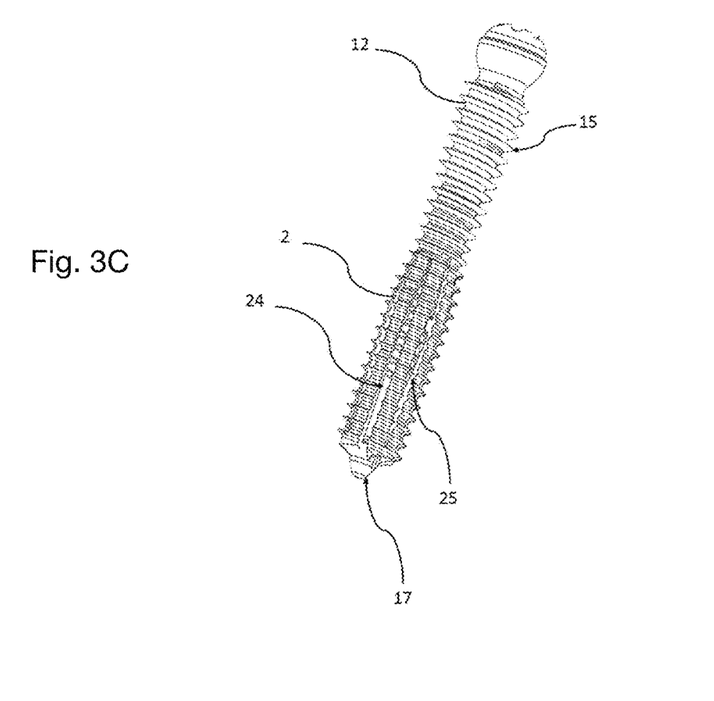
FIG. 3C represents a diagram of the osseous implant after the expansion according to the invention.
Figure 4A:
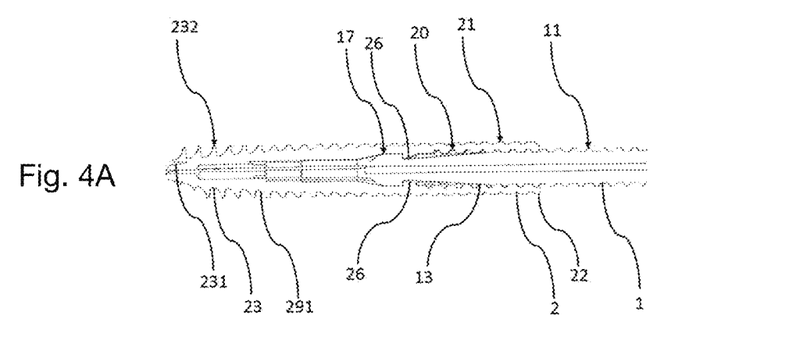
FIG. 4A and FIG. 4B represent a view of the interior of the osseous implant before the expansion of the sleeve according to the invention.
Figure 4B:
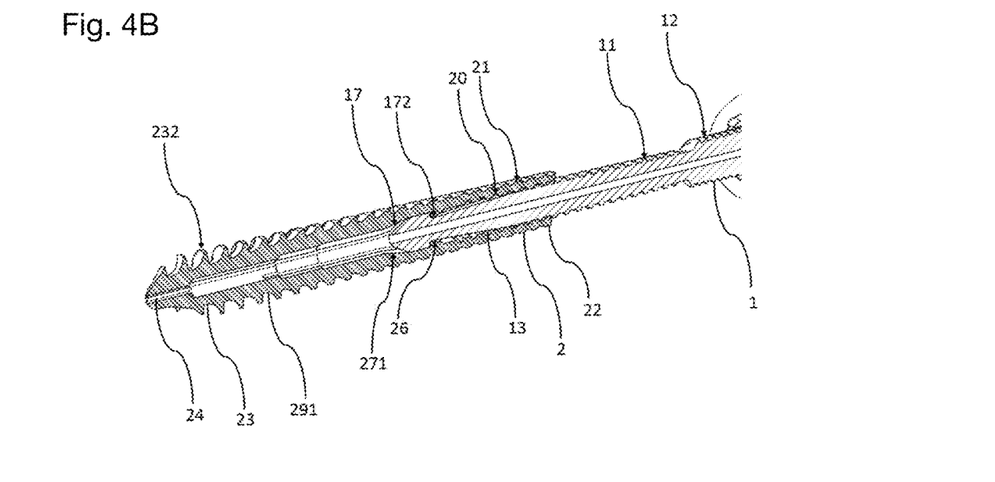
Figure 5:
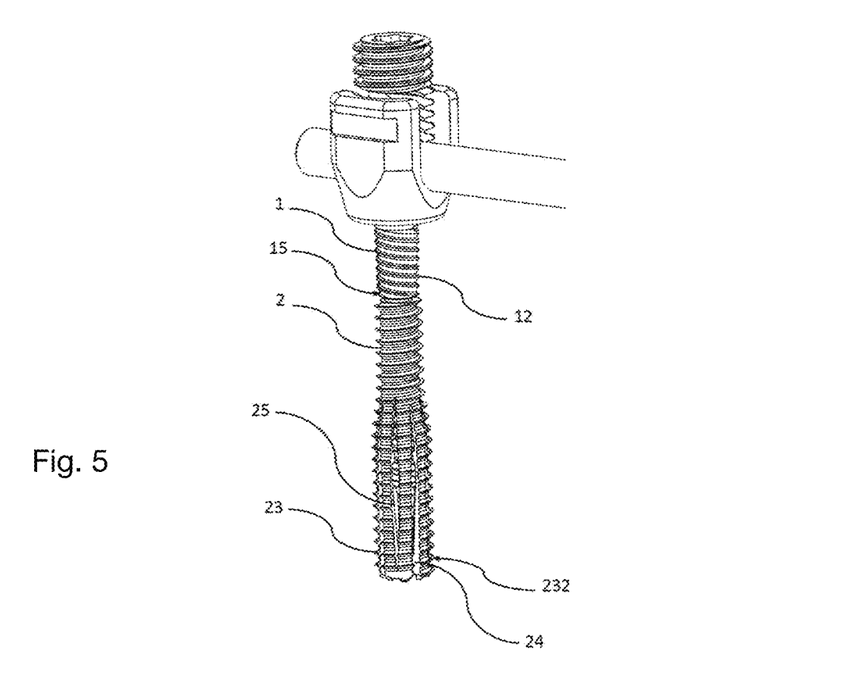
FIG. 5 and FIG. 6 represent a diagram of the osseous implant after the expansion of the sleeve according to the invention.
Figure 6:
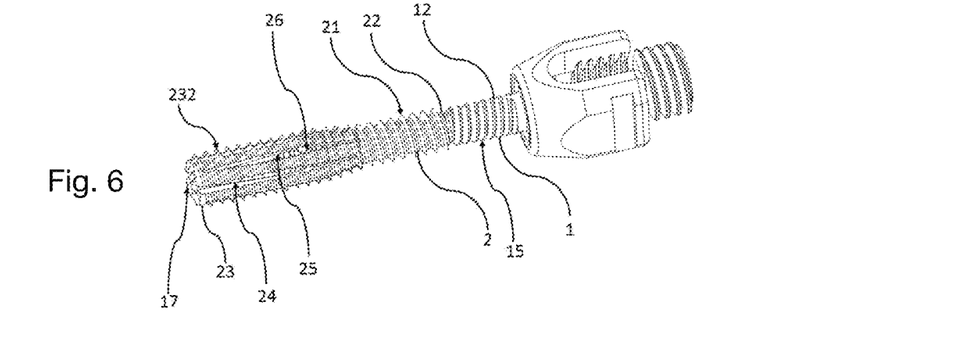
Figure 7:
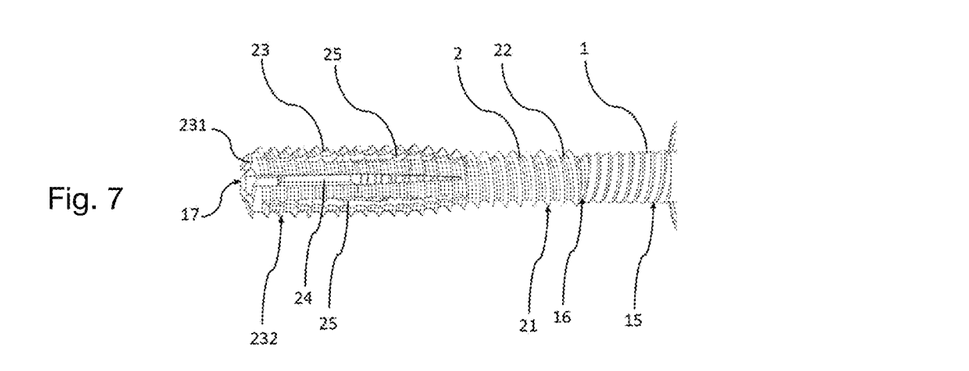
FIG. 7 and FIG. 8 represent a diagram of the sleeve in the expanded position according to the invention.
Figure 8:
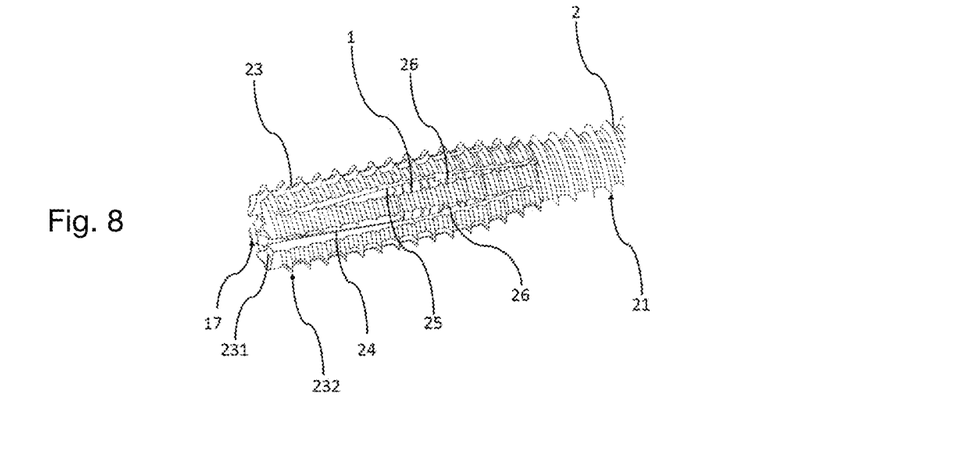
Figure 9A:
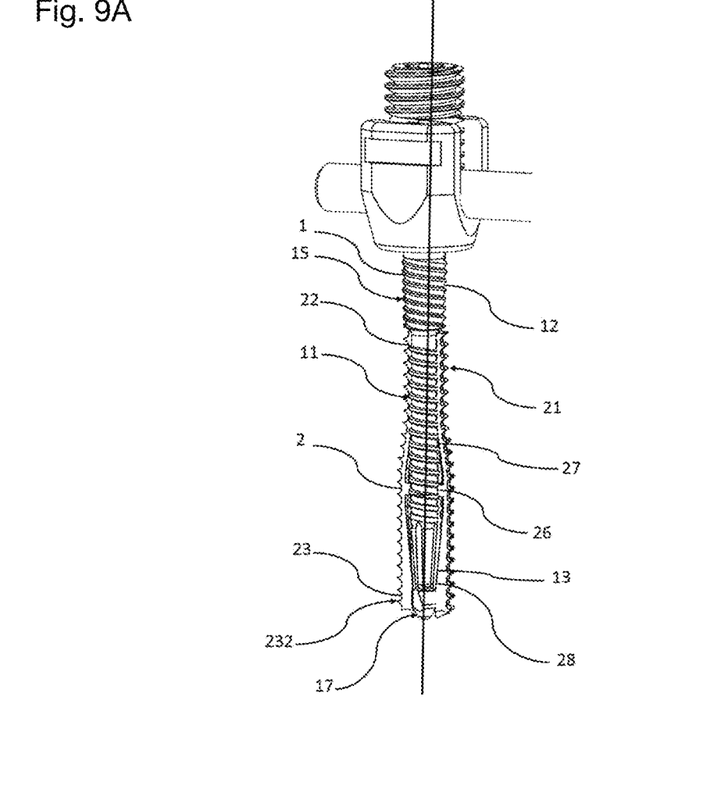
FIG. 9A and FIG. 9B represent a diagram of the interior of the osseous implant after the expansion of the sleeve according to the invention.
Figure 9B:
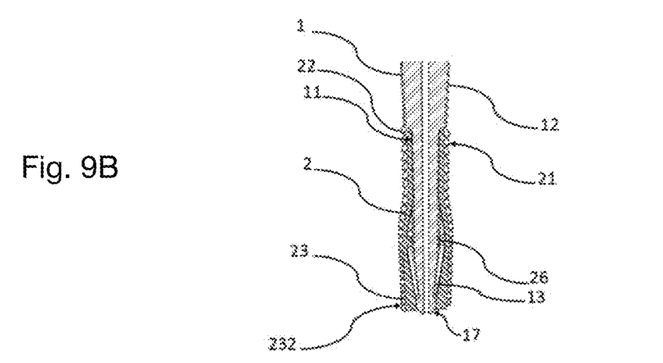
Figure 10A:
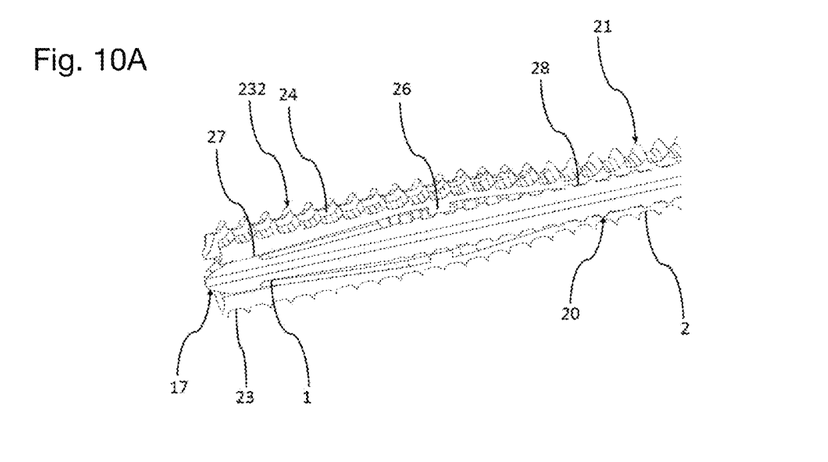
FIG. 10A and FIG. 10B represent a diagram of the interior of the sleeve in the expanded position according to the invention.
Figure 10B:
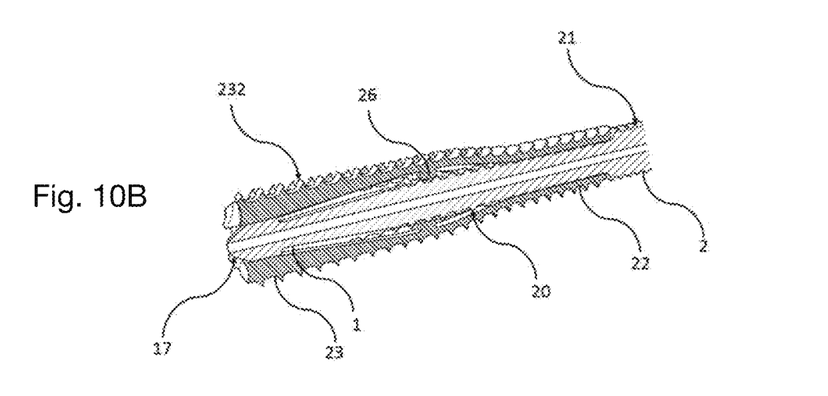
Figure 11:
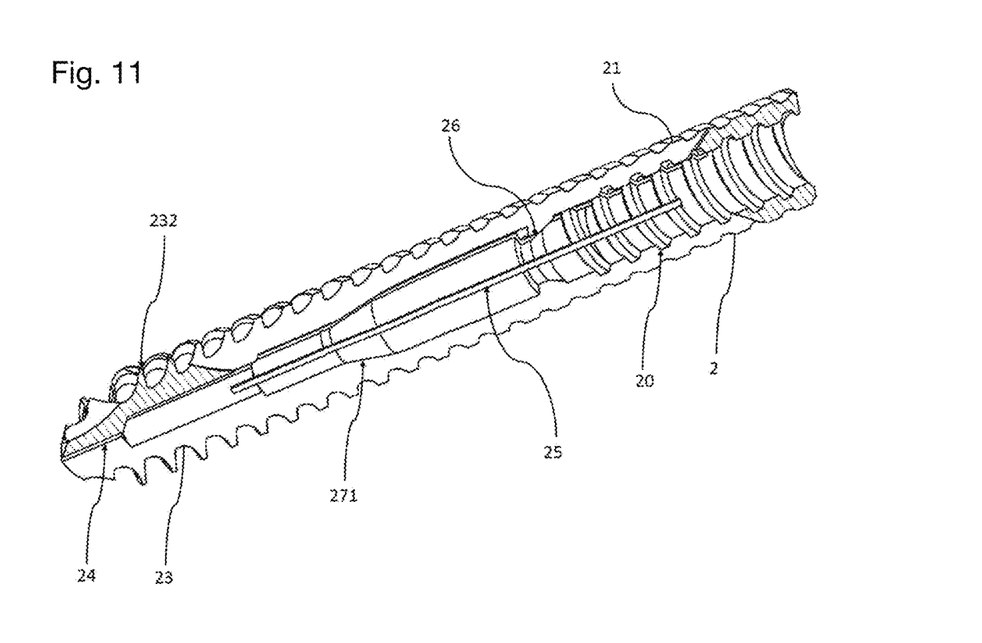
FIG. 11 represent a diagram of a cross-section of the interior of the osseous implant, before the expansion according to the invention.

In some embodiments, the expandable sleeve (2) has a domed shape at the central bearing point, as for example represented in FIG. 3C, by the presence of the angles α and β.

In some embodiments, as for example represented in FIG. 3A to FIG. 3C, FIG. 5 to FIG. 8, the expandable sleeve (2) includes longitudinal through-slots (24) extending up to its distal portion (23) and longitudinal non-through slots (25) allowing the expansion of the expandable sleeve (2). It is preferable that there are several through (24) or non-through (25) slots, and that the distal portion (23) includes the two types of slots, that is to say longitudinal through slots (24) and longitudinal non-through slots (25).

In some embodiments, the synergy between the through-slots (24) and the non-through slots (25) also allows truncated cone geometry.

In some embodiments, the non-through slots (25) allow the expandable sleeve (2) to expand in the cancellous osseous tissue by presenting a domed shape, of the convex type, making it possible to compress and densify the material over its periphery, thus improving primary stability, healing, and making it possible to avoid the addition of cement to stabilize and immobilize the osseous implant.

In some embodiments, there are as many self-tapping notches (231) as there are longitudinal through-slots (24).

In some embodiments, the through-slots (24) and the non-through slots (25) are positioned offset relative to each other over the length of the expandable sleeve (2). The offset of the through-slots 24 and non-through slots 25 over the length improves the flexibility and the mechanical strength of the expandable sleeve (2) during the expansion.

In some embodiments, the longitudinal through (24) and non-through (25) slots on the distal portion (23) allow the cylindrical expansion of the expandable sleeve (2). The longitudinal non-through slots (25) contribute to the stability of the osseous implant in the osseous tissue by allowing, during the expansion, to be able to maintain the contact profile on the three bearing points between the expandable sleeve (2) and the screw (1), and by allowing the forces due to the expansion to be uniformly distributed over the periphery of the expanded expandable sleeve (2). The longitudinal through (24) and non-through (25) slots allow a radial expansion of the proximal portion (22) of the expandable sleeve (2) by complying with the elastic limit of the material of the expandable sleeve (2) and its elastic shrinking during the unscrewing.

In some embodiments, said longitudinal through-slots (24) extend over 10 to 90% of the length of the expandable sleeve (2).

It should be noted that a bone growth passes through the interstices inside the osseous implant which consist in the through-slots (24) and the non-through slots (25). The bone regrowth contributes to the immobilization and to the stability of the implant in the osseous tissue, but also makes it more difficult to remove the implant when an ablation is necessary after several months of implantation in the osseous tissue.

In some embodiments, the distance marker (16) is a laser marker.

In some embodiments, the osseous implant is removed from the osseous tissue, without generating serious lesions or significant cracks in the bone thanks in particular to the elastic deformation of the expandable sleeve (2) within the limit of the elasticity of the material used.

Figure 12:
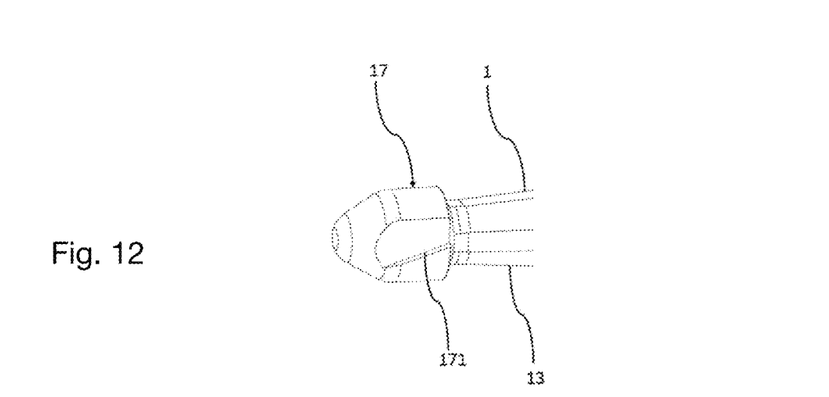
FIG. 12 represents a diagram of the screw tip according to the invention.

As represented for example in FIG. 12, the head (17) comprises at least one notch of the rear flute (171) type for milling the bone, in order to mill or tap the bone during the extraction of the osseous implant. Indeed, after insertion of the implant in the cancellous part of the bone, the osseous tissue is reformed by becoming harder around the implant and in the interstices left empty in the slots that have opened and/or between the inner wall of the expandable sleeve (2) and the outer wall of the screw (1) after the expansion. It is then necessary to mill or tap the hard part of the bone to be able to move the implant and unscrew it during the extraction, in order to remove the osseous implant.

In some embodiments, additional short screwing allows breaking the osseous tissue reformed around the implant in order to unblock the latter, followed by an unscrewing which then allows removing the implant.

In some embodiments, during the ablation of the osseous implant, the rear flutes (171) allow milling or tapping the bone which has formed between the screw (1) and the expandable sleeve (2), during the receding of the screw (1) until returning to the rest position in which the external diameters are substantially constant over the entire length of the expandable sleeve (2). This return to constant diameter being automatic when the expandable sleeve (2) has an elastic deformation, while when the expandable sleeve (2) has a plastic deformation, this return to constant diameter will be imposed by the compression undergone by the expandable sleeve (2) during removal at the outlet of the duct created by the implant.

In some embodiments, the rear flutes (171) have a cutting edge. The cutting edge of said rear flute (171) has an angle, relative to the longitudinal axis (L), determined by the thread direction the screw (1) when the implant is removed.

The extraction the osseous implant comprises the following steps:

Unscrewing the osseous implant in the direction of the external threading (11) until the appearance of the distance marker (16), Locking the implant by a clamp blocking the screw (1) in the expandable sleeve (2) in the rest position, Unscrewing the implant in the direction of the second threading (21).

The osseous implant proposed in the invention can therefore be extracted from the osseous tissue quickly and accurately, its removal being facilitated and/or the risks of damaging the bone during its removal being limited.

The present application describes various technical characteristics and advantages with reference to the figures and/or to various embodiments. Those skilled in the art will understand that the technical characteristics of a given embodiment can indeed be combined with characteristics of one or more other embodiment(s) unless the reverse is explicitly mentioned or these characteristics are incompatible or the combination does not work.

More generally, combinations of various types of implant retaining means and/or spine retaining means are envisaged and will be appreciated by those skilled in the art using the functional and structural considerations provided in the present application. In addition, the technical characteristics described in a given embodiment can be isolated from the other characteristics of this mode unless the reverse is explicitly mentioned, in particular because the functional considerations provided in the present application will provide a sufficient explanation so that the structural adaptations possibly necessary are within the reach of those skilled in the art.

Those skilled in the art, upon reading the present application, will understand that embodiments in many specific forms other than those described in detail are possible without departing from the field of application of the invention as claimed. Therefore, the present embodiments should be considered by way of illustration, but can be modified in the field defined by the scope of the appended claims, and the invention should not be limited to the details given above.

The invention claimed is:

1. An osseous anchoring implant with facilitated extraction, comprising:
    an expandable sleeve extending between a proximal portion having a first internal diameter, and a distal portion having a second internal diameter smaller than said first internal diameter, these two portions defining a longitudinal axis and said first and second internal diameters defining an internal profile of said expandable sleeve, and comprising at least a first threading inside the expandable sleeve and, at least a second threading outside the expandable sleeve,
    a screw extending between a proximal portion and a distal portion on an axis collinear with the axis and having along said longitudinal axis, an external profile complementary to said internal profile of said expandable sleeve and, at least one external threading whose screw pitch is reversed relative to said second external threading of the expandable sleeve,
    the implant being able to switch from a folded rest position to a deployed position by the actuation of said reversed threading by causing the penetration of the screw into the expandable sleeve and generating the expansion of said expandable sleeve by deformation, thanks to the fact that the external diameter of the screw is greater, at least on a distal portion, than said second internal diameter of the expandable sleeve,
    in the deployed position of the implant, the second internal diameter of the expandable sleeve being greater than or equal to the first internal diameter,
    wherein the
    distal portion of the screw includes a head comprising at least one rear flute with a cutting edge to mill the bone during the extraction of the osseous implant and facilitate the removal of the implant.

2. The implant according to claim 1, wherein the cutting edge of said rear flute has an angle, relative to the longitudinal axis, determined by the thread direction of the screw when the implant is removed.

3. The implant according to claim 1, wherein the internal diameter of the expandable sleeve comprises, at the distal portion, at least a shrinkage having a size inferior to the external diameter of the screw.

4. The implant according to claim 3, wherein the at least one shrinkage is located at a distance from the proximal portion along the longitudinal axis determined as a function of the depth, in the osseous tissue, at which the expansion of the expandable sleeve is desired.

5. The implant according to claim 1, wherein the implant comprises an outer osseous anchoring threading on a frustoconical portion whose flaring is reversed relative to the flaring formed by the truncated cone of the sleeve in the deployed position.

6. The implant according to claim 1, wherein said expandable sleeve includes longitudinal through-slots extending up to its distal portion.

7. The implant according to claim 6, wherein the distal portion of the sleeve is self-tapping thanks to the fact that it includes at least one notch or flute.

8. The implant according to claim 7, wherein there are as many self-tapping notches or flutes as there are longitudinal through-slots.

9. The implant according to claim 1, wherein said expandable sleeve includes longitudinal non-through slots.

10. The implant according to claim 1, wherein the screw comprises at least one distance marker to visualize the moment when the screwing of the screw in the expandable sleeve must be carried out in the opposite direction to the screwing the expandable sleeve into the osseous tissue.

11. The implant according to claim 10, wherein said at least one distance marker is a laser marker.

12. The implant according to claim 1, wherein the expandable sleeve is made of plastic or elastic material.

13. A method for extracting an implant according to claim 1, the method comprising the following steps:
  unscrewing the implant in the direction of the external threading until the appearance of a distance marker,
  locking the implant by a clamp blocking the screw in the expandable sleeve in the rest position,
  unscrewing the implant in the direction of the second threading.

14. The extraction method according to claim 13, the method comprising an additional screwing before unscrewing the implant.

\* \* \* \* \*